(12) United States Patent
De Mari et al.

(10) Patent No.: US 10,071,102 B2
(45) Date of Patent: Sep. 11, 2018

(54) INJECTABLE MIRTAZAPINE FOR TREATING APPETITE LOSS AND NUTRITIONAL DISORDERS IN CATS

(71) Applicant: VIRBAC, Carros (FR)

(72) Inventors: Karine De Mari, Carros (FR); Annaele Sanquer, Nice (FR)

(73) Assignee: VIRBAC, Carros (FR)

( * ) Notice: Subject to any disclaimer, the term of this patent is extended or adjusted under 35 U.S.C. 154(b) by 0 days.

(21) Appl. No.: 15/105,172

(22) PCT Filed: Dec. 18, 2014

(86) PCT No.: PCT/IB2014/067079
§ 371 (c)(1),
(2) Date: Jun. 16, 2016

(87) PCT Pub. No.: WO2015/092738
PCT Pub. Date: Jun. 25, 2015

(65) Prior Publication Data
US 2016/0310504 A1 Oct. 27, 2016

(30) Foreign Application Priority Data
Dec. 20, 2013 (FR) .................................... 13 63226

(51) Int. Cl.
| | | |
|---|---|---|
| *A61K 31/55* | (2006.01) | |
| *A61K 9/00* | (2006.01) | |
| *A61K 9/08* | (2006.01) | |
| *A61K 47/12* | (2006.01) | |

(52) U.S. Cl.
CPC ............ *A61K 31/55* (2013.01); *A61K 9/0019* (2013.01); *A61K 9/08* (2013.01); *A61K 47/12* (2013.01)

(58) Field of Classification Search
CPC .......... A61K 31/55; A61K 47/12; A61K 9/08; A61K 9/0019
See application file for complete search history.

(56) References Cited

U.S. PATENT DOCUMENTS

2013/0274247 A1* 10/2013 Quimby ................ A61K 31/55
514/214.02

FOREIGN PATENT DOCUMENTS

| WO | 01/00196 A2 | 1/2001 |
| WO | 2013/158130 A1 | 10/2013 |

OTHER PUBLICATIONS

International Search Report dated Mar. 5, 2015 corresponding to International Patent Application No. PCT/IB2014/067079, 8 pages.
Avis, K.E., et al., "Parenteral Preparations," Chapter 41, A. R. Gennaro: Remington: the science and practice of pharmacy, 20ty Edition, 2000, Lippincott, Baltimore, MD US. XP002728555, pp. 780-786.
Voigt, R.M., et al., "Repeated mirtazapine nullifies the maintenance of previously established methamphetamine-induced conditioned place preference in rats," Behavioural Brain Research, Elsevier, Amsterdam, NL, vol. 225, No. 1, Jul. 2011, pp. 91-96.
Quimby, J.M., et al., "Mirtazapine as an appetite stimulant and anti-emetic in cats with chronic kidney disease: A masked placebo-controlled crossover clinical trial," The Veterinary Journal, Elsevier, vol. 197, No. 3, Sep. 2013, pp. 651-655.
Rouini, Mohammad-Reza, et al., "Pharmacokinetics of mirtazapine and its main metabolites after single intravenous and oral administrations in rats at two dose rates," DARU Journal of Pharmaceutical Sciences, Biomed Central Ltd, London, UK, vol. 22, No. 13, 2014, pp. 1-5.

* cited by examiner

Primary Examiner — Sudhakar Katakam
(74) *Attorney, Agent, or Firm* — Dentons US LLP

(57) ABSTRACT

Described herein is a method of administering mirtazapine via the parenteral route to treat the decrease or loss of appetite and/or other disorders induced by undernutrition in cats.

12 Claims, 1 Drawing Sheet

Figure 1:
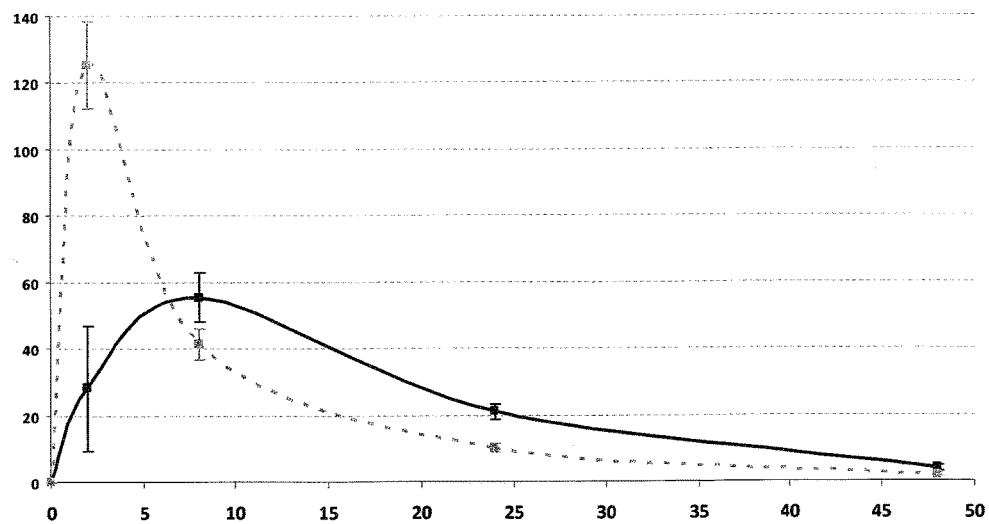

INJECTABLE MIRTAZAPINE FOR TREATING APPETITE LOSS AND NUTRITIONAL DISORDERS IN CATS

CROSS-REFERENCE TO PRIOR APPLICATIONS

This application is a National Stage of PCT/IB2014/067079, filed Dec. 18, 2014, and designating the United States (published in on Jun. 25, 2015, as WO 2015/092738A1), which claims priority under 35 U.S.C. § 119 to French Patent Application No. 1363226, filed Dec. 20, 2013, each hereby expressly incorporated by reference in its entirety and each assigned to the assignee hereof.

The present invention relates to the veterinary field and the object thereof relates in particular to the development of medicinal products for the treatment of anorexia in animals.

The cat is an animal that is particularly prone to anorexia, a disorder that can manifest itself in several contexts; it may for example result from the sudden changing of the foods that are provided, from situations that are stressful for the animal, from environmental changes, or the natural aging of the animal. Anorexia is also a clinical manifestation that frequently accompanies various health conditions and disorders in cats. While the element that triggers the anorexia needs to be diagnosed and treated, it is also important to quickly help the animal to resume a normal diet in order to avoid causing aggravation of its pathology and prevent the occurrence of other disorders. In addition, the presence of pain regardless of the cause (dental pain, shock, acute or chronic musculo-skeletal disorders, etc), of nausea and/or vomiting (as a result of taking certain medicines or of motion sickness for example), of partial physical discomfort that complicates the access to food (presence of a collar, a cast or bandage), a behavioural disorder (such as anxiety, depression, dementia, phobia, food aversion), will likely bring about anorexia. Finally, anorexia is a disorder that is commonly observed during a period of hospitalisation and more particularly during the postoperative period; there again, it is important for the animal to quickly resume a normal diet to help in its recovery.

Cats usually tend to regain their appetite when the causes of stress are removed and when there is improvement in their comfort level; however, this is not always sufficient. It then becomes important to implement a drug treatment that stimulates the appetite and provides for the return to a normal diet.

Mirtazapine (±)-1,2,3,4,10,14b-hexahydro-2-methyl-pyrazino-(2,1-a)-pyrido-(2,3-c)-benzazepine) is one of the various active ingredients used for the treatment of animal anorexia; it has the following chemical structure:

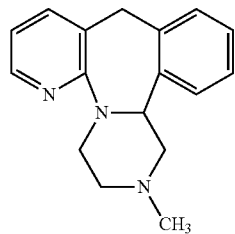 [SMILES: CN1CCN2c3ncccc3Cc3ccccc3C2C1]

and is mainly used as an antidepressant in human medicine.

The team of Quimby et al. have carried out several studies on the pharmacokinetics and the pharmacodynamics of mirtazapine administered orally at a dose of 1.88 mg or 3.75 mg in cats in which they have deemed the effects to be satisfactory (Quimby et al. Journal of Veterinary Pharmacology and Therapeutics [J. vet. Pharmacol. Therap.] 34, 388-396, 2010; Journal of Veterinary Internal Medicine [J. Vet. Intern. Med.]2011; 25; 985-989; The Veterinary Journal [The Vet. Journal], 2013; WO2013/158130); in addition, the authors explain their reluctance to administer mirtazapine by the intravenous route because they do not expect an interesting beneficial effect, given moreover, that this route of administration has never been explored and could likely cause undesirable adverse effects.

However, it is difficult to administer a medicament orally to an animal especially if the latter totally refuses to partake of food.

In this context, the Applicant has put forward strong evidence demonstrating that the administration of mirtazapine via the parenteral route effectively stimulates the appetite in animals and presents favourable pharmacokinetic data as compared to the oral administration thereof.

Thus, the present invention relates to Mirtazapine (1,2,3,4,10,14b-hexahydro-2-methylpyrazino(2,1-a)pyrido(2,3-c)benzazepine) for use thereof for the treatment of the decrease or loss of appetite and/or the prevention of disorders induced by undernutrition in an animal, characterised in that the mirtazapine is administered via the parenteral route (subcutaneous, intramuscular, intradermal, intravenous).

In the present case, the mirtazapine injection offers the following advantages:
it presents a good level of local tolerance;
administered in this way, the mirtazapine produces an effect that is less dependent on the state of health of the animal and therefore has greater reproducibility and reliability;
this mode of administration avoids the administration of the medicine by gavage, a method that is particularly delicate and difficult to perform on cats that are anorexic and/or in a nauseous state.
in an unexpected manner, the pharmacokinetics of mirtazapine has proven to be advantageous because it is slower and produces a prolonged or sustained effect;
the maximum (or peak) plasma concentration (Cmax) is lower, which thus avoids the risks of overdosing and/or intolerance; this is particularly advantageous in respect of mirtazapine which is known to have toxic effects on the liver;
it provides the ability to easily adjust the dose according to the weight of the cat (dose adjustable in mg/kg) which thereby makes it possible to optimally develop both an effective dose as well as a good level of systemic tolerance;
finally, unlike administration via the oral route, parenteral administration limits the effect of hepatic first pass metabolism thereby reducing the problems related to intolerance, metabolisation or toxicity.

This use of mirtazapine is intended to cover all domestic or companion animals (including rodents), in particular domestic carnivorous animals (such as cats, dogs and ferrets). More specifically, the animal of interest to be treated is a feline, in particular a cat such as an Abyssinian cat, the long-haired Abyssinian cat, the American short-haired cat, American hard-haired cat, American Bobtail, American Curl, American Shorthair, American Wirehair, Angora, Turkish Angora, Asian, Australian Mist, Balinais, Traditional Balinais, Balinese, Bengal, Bengali, Birman, Russian Blue, American Bobtail, Japanese Bobtail, Russian Bobtail, Bombay, British Longhair, British Shorthair, Burmese, Burmilla, Calif. Rex, California Toyger, Californian Spangled, Celtic, Ceylan, Chantilly/Tiffany, Chartreux, Poodle Cat, Ceylon Cat, Alley Cat, Isle of Man Cat, House Cat, Siberian Cat, Norwegian Wood Cat, Norwegian Forest Cat, Sri Lanka Cat, Naked/Hairless Cat (Chat Nu), Siamese Cat (Royal Cat of Siam), Turkish Van (Lake Van) Cat, Chausie, Colourpoint Shorthair, Cornish Rex, Cymric, Devon Rex, Don Bald Cat, Don Hairless, Don Sphynx, Donskoy, Egyptian Mau, European Shorthair, European, Exotic Shorthair, Short-haired Exotic, Foldex, Gatto di Ceylon, German Rex, Havana Brown, Highland Fold, Highland Straight, Japanese Bobtail, Javanese, Korat, Kurile Islands Bobtail, Kurilian Bobtail, Laperm, Lynx Domestic, Maine Coon, Malayan (Asian), Mandarin, Manx, Egyptian Mau, Munchkin, Nebelung, Neva Masquerade, Norwegian, Norwegian Forest Cat, Ocicat, Ojos Azules, Oriental Long-haired, Oriental Shorthair, Persian, Peterbald, Petersburg Sphynx, Pixie Bob, Pudelkatze, Ragdoll, Rex Cornish, Rex Devon, Rex Selkirk, Russian, Russian Bobtail, Russian Hairless, Sacred Cat of Burma, Safari, Savannah, Scottish Long-haired, Scottish Fold, Scottish Straight, Selkirk Rex, Serengeti, Seychelles, Si-Sawat, Siamese (Old Style), Siamese (Modern), Traditional Siamese, Siberian, Silver Laces, Singapura, Skogkatt, Snow Shoe, Sokoke, Somali, Californian Spangled, Sphynx, Spotted Mist, Thai, the Dalles La Perm, Tiffanie, American Tiffany, English Tiffany, Tonkinese, Tonkinese, Toyger, Turc Van, Turkish Angora, Turkish Van, York Chocolate.

The claimed use according to the invention is more particularly suited to the cat breeds which present predispositions to polycystic kidney disease, a pathology that is often linked to a decrease in appetite, and even to anorexia; it concerns the cat breeds Maine Coon, Abyssinian, Siamese, Russian Blue, Himalayan, and Burmese. This use is more particularly suited for cats aged 7 or more years, and preferably aged 9 or more years, in whom renal insufficiency or failure is more frequent and causes regular loss of appetite.

The use according to the present invention serves the object of treating the decrease or loss of appetite, in particular, of stimulating the appetite and/or treating anorexia and/or a food aversion; and/or of preventing and/or treating a nauseous state and/or vomiting; and/or of preventing disorders induced by undernutrition in an animal, including weight loss, resistance to insulin, glucose intolerance, liver lipidosis, etc.

In cats, undernutrition or malnutrition is generally characterised by a body condition score (BCS) of less than 3 out of 5; a loss of weight that is greater than 5% in one month or 10% in 6 months; anorexia of more of three days; a generalised amyotrophy and hypoalbuminemia (L. Yaguiyan-Colliard, Congrès de l'AFVAC [Association Française des Vétérinaires pour Animaux de Campagnie] 2009/2009 AFVAC [French National Association of Veterinarians for Companion Animals] Congress in Lille).

The use of mirtazapine according to the invention offers a significant benefit of interest for the treatment of the decrease or loss of appetite and/or post-operative undernutrition; indeed, it is frequently observed that a cat that has undergone a surgical procedure is somewhat slow in regaining normal feeding habits. It is thus advantageous to remedy this condition by means of an injection of mirtazapine that is administered before or up to 72 hours after surgery and which presents an effective and sustained action, in order to help the animal to accelerate recovery during its convalescence. Quite obviously, if the said injection is not enough, it is possible to repeat the dose at least once, 2 to 7 days after the preceding injection. The pharmacokinetic profile of mirtazapine when injected proves to be particularly appropriate to post-operative anorexia: at the end of the clinical observation period that follows an intervention, where the veterinarian were to note that the animal had been slow to resume feeding, they could administer an injection of mirtazapine to the latter. The sustained effect observed with this mode of administration avoids having to go too frequently to the veterinarian if administration of further doses of medicament were to become necessary.

According to one particular embodiment of the invention, it relates to mirtazapine for use thereof for the treatment or prevention of anorexia in domestic carnivorous animals characterised in that the mirtazapine is formulated in the form of an injectable medication which represents an administered volume that is less than or equal to 3 ml and the injection of which produces an effect lasting at least 48 hours.

Mirtazapine is formulated in an injectable liquid composition which preferably includes a carrier that is constituted primarily by a solvent, that is to say water, an organic solvent or the mixture of these two, or a plant-based (vegetable) oil, an organic solvent or the mixture of these two, or even the mixture of water with a plant oil. By way of a variant of the invention, the carrier is constituted by a mixture of plant oil and a solvent; the solvent then represents from 0 to 30% of the solvent/plant oil mixture.

Among the plant or vegetable oils, mention may be made for example, of palm oil, corn oil, cottonseed oil, sunflower oil, peanut oil, olive oil, soybean oil, safflower oil, coconut oil, sesame oil; or among the semi-synthetic plant oils obtained by fractionation and/or hydrolysis and/or total esterification of natural plant oils such as for example the triglycerides of fatty acids derived from plant oils, like the triglycerides of Caprylic acid, capric acid, linoleic acid, succinic acid (sold under the trade names Miglyol® 810, 812, 818, 820, 829), esters of propylene glycol and fatty acid derived from plant oil like the esters of propylene glycol, and caprylic and capric acids (sold under the trade names Miglyol® 840), as well as the mixture thereof, as well as esters including therein Triacetin (glyceryl triacetate), and ethyl oleate, for example.

Among the organic solvents, mention may be made for example, of benzyl alcohol, ethanol, N-methyl pyrrolidone, glycerol formal, glycofurol, Diethylene glycol monoethyl ether, propylene glycol, polyethylene glycol, for example, PEG 300, PEG 200, and PEG 400.

The selection of the carrier is done, in a manner so as to form liquid solutions, based on its ability to dissolve the active substance at ambient temperature without modifying the chemical structure and stability. The carrier selected should be biocompatible and suitable for the injectable route. The carrier is to be selected from among the polar protic solvents, polar aprotic solvents, apolar aprotic solvents, or the mixture thereof.

According to one particular embodiment of the invention, the mirtazapine is in solution in the injectable liquid veterinary composition.

The injectable liquid composition of mirtazapine may also include at least one antioxidant selected from amongst butylhydroxyanisole (BHA), butylhydroxytoluene (BHT), vitamin E and derivatives thereof, propylgallate and the mixtures thereof.

The injectable liquid composition includes the mirtazapine at a concentration less than or equal to 2% w/v (weight/volume), preferably comprised between 0.5% and 1.5% w/v, even more preferentially comprised between 0.15% and 1% w/v; this injectable liquid mirtazapine composition is administered at a volume that does not exceed 3 ml, it is preferably less than or equal to 2 ml and more preferentially comprised between 0.5 ml and 1 ml.

The administration of the injectable liquid mirtazapine composition is such that it will enable the administration of a dose of mirtazapine comprised between 0.2 mg/kg and 2 mg/kg, more particularly between 0.2 mg/kg and 1.5 mg/kg, or between 0.2 mg/kg and 0.5 mg/kg, or even between 0.5 mg/kg and 1 mg/kg, or even more preferentially between 0.4 mg/kg and 0.8 mg/kg.

The injectable liquid composition of mirtazapine is preferably administered in one single dose; alternatively, it is administered multiple times, preferably in two doses, with the doses being spaced out from 1 to 7 days apart, or from 2 to 7 days apart, preferably from 2 to 5 days apart, or in a more appropriate manner the two injections will be separated by an interval of 24 hours, 48 hours or 72 hours, although the present invention is not limited to the administration or dosing regimen indicated here above.

FIGURES

FIG. 1 is a graph that represents the plasma concentration of mirtazapine in ng/ml (nanogram/milliliter) over the course of time (in hours) in a healthy cat following a dose administered by injection (black curve) and after a dose administered via the oral route (dashed gray curve).

Figure 2A:
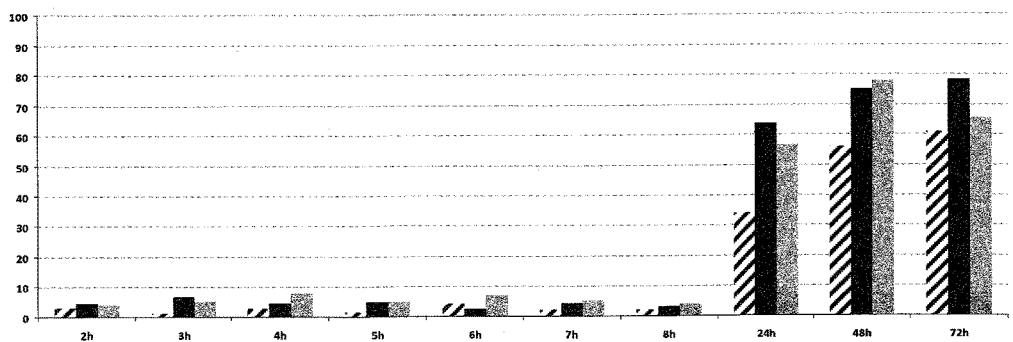
Figure 2B:
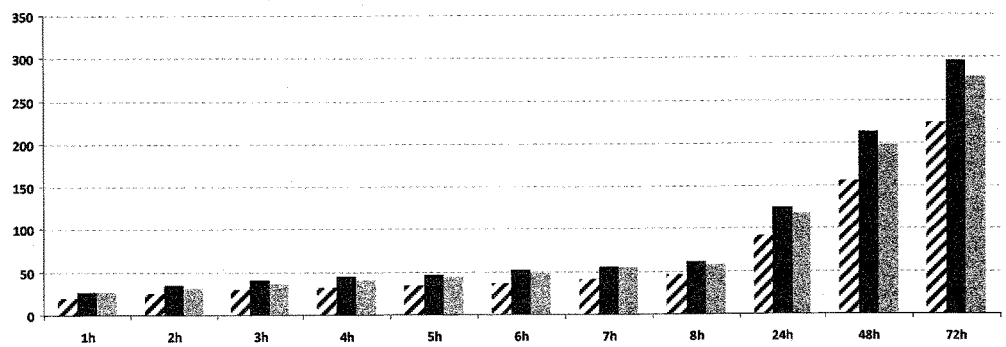

FIGS. 2A and 2B are histograms representing the food consumption, post-treatment, in grammes over time (in hours, at the time of measurement for 2A, and on a cumulative basis for 2B) of cats who have been subjected to a stress. The striped histograms correspond to the control group, the black histograms correspond to the group that received the product via injectable administration route according to the invention, the grey histograms correspond to the group that received the product via the oral administration route in accordance with the prior art.

EXAMPLE—TESTING OF ADMINISTRATION OF MIRTAZAPINE BY INJECTION ON HEALTHY CATS

The purpose of these tests is to evaluate the effect of administration of mirtazapine by subcutaneous injection on the appetite of cats as compared to dose administration by the oral route (positive control) and a control (injection of saline solution, negative control).

These tests were conducted in accordance with good laboratory practices laid down by the "US Animal Welfare Act" and the guidelines of the "Canadian Council on Animal Care".

Materials and Methods

Products Administered

The injectable formulation tested is a suspension of mirtazapine at a concentration of 0.75% weight/volume of Miglyol 812. The oral formulation tested is a solution of mirtazapine at 15 mg/ml (Summit Veterinary Pharmacy Inc).

Protocol

The healthy cats selected were previously acclimated for at least seven days prior to testing; during this period, they were examined by a veterinarian. They were then divided into three groups of two cats each according to a cross-over experimental design, with each cat receiving each of the 3 treatments according to a predetermined sequence:

0.5 ml of saline (0.9% sodium chloride) was administered by subcutaneous injection in the interscapular area to the T0 group which represents the negative control;

the group T1 received a subcutaneous injection, in the interscapular area, of 0.5 ml of the tested formulation of mirtazapine (represents a dose administration of 3.75 mg of mirtazapine);

the group T3 instead received 0.25 ml (represents a dose administration of 3.75 mg of mirtazapine) of the liquid formulation by means of forced administration (syringe) in the mouth and represents the positive control group.

In order to simulate a stress that would be likely to cause a loss of appetite in the cats, their environment had been modified regularly just prior to the start of the study.

The evaluation of the consumption of food by the cats was carried out by weighing of the ration provided (100 g) at t=0, 1, 2, 3, 4, 5, 6, 7, 8, 24 and 48 hrs after dose administration; if the ration was totally consumed, a new ration of 100 g was then provided.

The determination of the plasma concentration of mirtazapine was done on the blood samples collected at days-1, 0, 14, 28 and 42 and at 2, 8, 24 and 48 hrs from the administration of mirtazapine.

Résultats

Pharmacokinetics

The graph in FIG. 1 represents the plasma concentration of mirtazapine following a dose administration by injection (grey curve) and after a dose administration by oral route (black curve).

It is evident from this graph that the pharmacokinetics of the product changes significantly depending on the mode of administration; the injection leads to a lower $C_{max}$ value and a longer $T_{max}$ value in comparison to oral administration, resulting in a profile that is more favourable in terms of duration of action and toxicity.

|  | Cmax (µg/L) | Tmax (h) | AUClast (µg/L * h) | Thalf (h) |
|---|---|---|---|---|
| Formulation injected | 58.25 | 9.25 | 1054.9 | 10.885 |
| Formulation ingested | 127.7 | 2 | 1047.7 | 8.8324 |

Local Tolerance

The examination of the points of injection of the product shows good local tolerance.

Food Consumption

The food consumption is represented in FIGS. 2A (food consumption measured at each point) and 2B (cumulative food consumption).

These tests demonstrate the more significant sustained effect of the injection as compared to the oral administration in particular from 72 hrs after the administration of mirtazapine. It is therefore interesting to note that the administration of a dose of mirtazapine by subcutaneous injection is as effective as the administration of the same dose by oral route with respect to inducing an increase in appetite, but that the injection presents the advantage of inducing appetite for a longer time period; this efficacy therefore has greater sustainability.

The invention claimed is:

1. A method of treating a decrease or loss of appetite and/or a disorder induced by undernutrition in a cat, the method comprising administering an effective amount mirtazapine to the cat via a parenteral route, wherein the mirtazapine is formulated as an injectable liquid veterinary composition, said composition comprising a plant-based (vegetable) oil, or a mixture of a plant-based (vegetable) oil and a solvent selected from the group consisting of water, an organic solvent or a mixture of water and organic solvent.

2. The method according to claim 1, wherein the mirtazapine stimulates the cat's appetite.

3. The method according to claim 1, wherein the disorder being treated is at least one disorder selected from the group consisting of anorexia, a nauseous state, vomiting, and food aversion.

4. The method according to claim 1, wherein the disorder is weight loss.

5. The method according to claim 1, wherein the decrease or loss of appetite and/or undernutrition are postoperative conditions.

6. The method according to claim 1, wherein the injectable liquid veterinary composition comprises a concentration of mirtazapine that is less than or equal to 2% weight/volume of the composition.

7. The method according to claim 1, wherein the injectable liquid veterinary composition comprises the mixture of the plant-based (vegetable) oil and the solvent selected from the group consisting of water, an organic solvent or a mixture of water and organic solvent, and wherein the solvent is in an amount from 0% to 30% of the solvent/plant oil mixture.

8. The method according to claim 1, wherein the mirtazapine is administered in an amount from 0.2 mg/kg to 2 mg/kg of the cat's body weight.

9. The method according to claim 1, wherein the mirtazapine is administered in an amount from 0.4 mg/kg to 0.8 mg/kg of the cat's body weight.

10. The method according to claim 1, wherein the mirtazapine is administered in one single dose.

11. The method according to claim 1, wherein the mirtazapine is administered in two doses separated by an interval of 24 hours, 48 hours or 72 hours.

12. The method according to claim 1, wherein the disorder being treated is anorexia in cats and wherein the mirtazapine is formulated as an injectable medication with an administered volume that is less than or equal to 3 ml.

* * * * *